United States Patent [19]

Bender et al.

[11] 4,353,989

[45] Oct. 12, 1982

[54] CHEMICAL SYNTHESIS APPARATUS FOR PREPARATION OF POLYNUCLEOTIDES

[75] Inventors: Robert Bender, Toronto; Peter D. Duck, Ottawa, both of Canada

[73] Assignee: ens Bio Logicals Inc., Toronto, Canada

[21] Appl. No.: 226,132

[22] Filed: Jan. 19, 1981

[51] Int. Cl.³ .............................................. C12M 1/00
[52] U.S. Cl. .................................. 435/287; 435/172; 435/317; 435/820
[58] Field of Search ........................ 435/172, 287, 317

[56] References Cited

PUBLICATIONS

New York Times, Thursday, Jan. 15, 1981, p. D2.
Chemical Week, Feb. 4, 1981, p. 52.

*Primary Examiner*—Robert J. Warden
*Attorney, Agent, or Firm*—Fleit & Jacobson

[57] ABSTRACT

An apparatus for the stepwise synthesis of polynucleotides in which the polynucleotide chains are extended in stepwise fashion from a modified form of polymer support to which the first unit is linked comprises a reaction column containing the polymer supported product and acting as the reaction vessel, and a series of reaction bottles all connected to the reaction column by means of a fluid flow conduit to which the vessels make connection via two-way valves arranged in series. The farthest upstream vessel of the series contains reaction solvent, used for washing purposes and the like. The most downstream of the reaction vessels contain nucleotide reagents. Each of the valves has two separate and discreet fluid flow passageways, the first of which is used exclusively for flow of reagent from its associated vessel into the fluid flow conduit, and the second of which is used exclusively for flow of solvent or reagents from an upstream vessel therethrough, thereby eliminating the possibilities of cross-contamination as a result of reagent residuals left in the dead space of the valve. The valves are biased towards their solvent flow condition. Materials are drawn through the fluid flow conduit and valves by suction, e.g. by means of a downstream pump.

9 Claims, 3 Drawing Figures

CHEMICAL SYNTHESIS APPARATUS FOR PREPARATION OF POLYNUCLEOTIDES

FIELD OF THE INVENTION

This invention relates to chemical synthesis apparatus, and more specifically to a form of chemical synthesis apparatus for production of polynucleotides by stepwise reaction of individual nucleotides to couple them to a polymer-supported growing polynucleotide chain.

BACKGROUND OF THE INVENTION AND PRIOR ART

The synthesis of polynucleotides is rapidly assuming commercial and industrial importance. Polynucleotides, comprising long polymeric chains consisting of deoxyribose or ribose sugar units linked to purine or pyrimidine base units, and joined into polymeric chains through phosphate linkages, are the chemical basis of nucleic acids. Segments of deoxyribonucleic acid (DNA), i.e. polynucleotide sequences, constitute genes, having encoded therein genetic information related to the sequence of the base units disposed along the polynucleotide chain. Recently, techniques have been developed for linking synthetic polynucleotide sequences into natural DNA, in bacterial cells and the like, so as to modify the genetic information of the cell, and hence to vary the chemical operation of the cell and the products which it is capable of producing. For example, the insulin producing gene has been totally synthesized, and this can now be spliced into bacterial cells to enable the cells to produce greater quantities of insulin by means of their ordinary biological function.

The structural units of DNA are deoxyribose sugar rings to which are linked one of the four purine or pyrimidine bases thymine, guanine, cytosine and adenine. Synthetic processes for making synthetic genes for splicing to DNA must involve the step by step coupling together of each of these four different units, in the desired, predetermined sequence. It is extremely important that the base sequences on all of the molecular chains be exactly correct, or genetic misinformation will be encoded into the synthetic gene, with potentially disastrous results when the gene is spliced into DNA in a cell.

Chemical synthesis of polynucleotides is a multistep, lengthy chemical process. In addition to individual chain extension steps, in which the next nucleotide unit of the sequence is coupled to the polynucleotide chain, the nucleotide reagents and the growing chain must be appropriately chemically protected to ensure that chemical reaction takes place at the correct location on the molecule. Additional process steps of protection and deprotection are therefore necessary.

There has recently been proposed (see U.S. patent application Ser. No. 06/149,685 Kelvin K. Ogilvie and Robert Bender, filed May 14, 1980) a solid state polynucleotide synthesis process, based upon solid polymer support for the growing polynucleotide chains. In this process, a first nucleotide unit is initially condensed with a modified, derivatized solid polymer such as silica gel, to form a coupled initial unit. Then the polymer-nucleotide intermediate is terminally deprotected, and the next nucleotide unit for the predetermined sequence is added to the polymer. These steps are repeated, to build up a polynucleotide chain of desired sequence and length. The process shows significant advantages for large scale operation, in that it can be conducted in a semi-automatic, semi-continuous fashion, with the polymer-polynucleotide growing chains as a solid column, and addition of reagents, solvents and the like sequentially to the column under predetermined conditions and for predetermined lengths of time, in sequence, to build the desired polynucleotide chain.

With the aforementioned polymer support-solid phase process, it is still very necessary to ensure that there is no cross contamination of reagents during the individual process steps. For example, if residues of the thymine-containing nucleotide are present in the reactor column during the stage of reaction when a cytosine nucleotide is supposed to be coupled to the growing polynucleotide chain, then some small proportion of the final polynucleotide chains will have incorrect sequences, and hence will encode incorrect genetic information. It is therefore necessary to provide a synthesis apparatus which substantially eliminates the possibility of any such cross contamination, even when emergency conditions arise, for use in preparation of synthetic genes.

SUMMARY OF THE INVENTION

It is an object of the present invention to provide a novel chemical synthesis apparatus.

It is a further object of the present invention to provide a chemical synthesis apparatus for the step-wise production of polynucleotides, using a solid polymer supported intermediate material.

It is a further object of the present invention to provide such an apparatus which substantially completely eliminates the possibility of cross contamination of reagents.

These and other objects of the present invention are accomplished by the provision of an apparatus having a reaction column in which the solid complex is contained and in which the reactions are conducted, and a single fluid flow conduit entering the reaction column. A plurality of reagent storage vessels are provided, each joined to the fluid flow conduit through the intermediary of a two-way valve. The valves are arranged in series along the fluid flow conduit, with the solvent containing reservoir being located furthest upstream from the reactor column, and the nucleotide reagent reservoirs being located most immediately upstream from the reaction column. Each of the two-way valves has two exclusive and discreet flow paths therethrough, one to be used solely for the supply of reagent from its associated reservoir into the fluid flow conduit, and the other to be used for straight through flow of materials from upstream reservoirs.

By means of the present invention, the possibility of having residues of the wrong nucleotide reagent in the reaction column during chain extension are effectively eliminated. The valves can be set, after each stage, to feed solvent through the fluid flow conduit, through all of the valves between each chain extension step. By suitable interlock means, it is arranged that only one of the said valves can be set into its reagent passage position at any given time. Whilst the reagent passageways in each individual valve may be left containing residual amounts of the said reagent when they are switched to the straight through position, this residual amount of reagent cannot enter the fluid flow line, since it is held in a discreet valve passageway, until that valve is returned to its reagent delivery condition in the predetermined cycle.

BRIEF REFERENCE TO THE DRAWINGS

In the accompanying drawings.

In the drawings, like reference numerals indicate like parts.

DESCRIPTION OF THE PREFERRED EMBODIMENTS

Preferably, all of the two-way valves are biased, e.g. by spring loading, towards their straight through flow condition, so that, in the event of a fault, power failure or the like, the system configuration is returned to a wash stage. The nucleotide reagent bases and other reagents are introduced into the reaction column by suction, e.g. by means of a pump located in the fluid flow conduit downstream of all of the two-way valves. The valves are arranged in series so that there is only one through path from the reservoirs to the pump functional at any time.

Preferably also, the reagent vessel include at least one separate vessel for containing and feeding deprotecting agent to the fluid flow conduit, for reaction with the growing polymer chains prior to addition of nucleotide for chain extension steps. There may also be included a re-cycle arrangement, whereby nucleotide reagent from the column may be re-cycled to its appropriate reagent storage vessel. For this purpose, it is preferred to provide a single re-cycle line, extending from the reaction column to a drain. This re-cycle line contains two-way valve connections, arranged in series, each valve being of the form previously described and arranged to return a nucleotide base to its appropriate reservoir, during chain extension step with that specific nucleotide reagent.

Most conveniently, the two-way valves are solenoid operated. They are conveniently all coupled to a microprocessor, into which the sequence of reactions can be programmed, along with their duration, so that the valves are operated automatically according to a predetermined sequence so as to produce the polynucleotide chains in the reaction column of the desired, predetermined sequence.

DETAILED DESCRIPTION OF THE SPECIFIC PREFERRED EMBODIMENT

Figure 1:
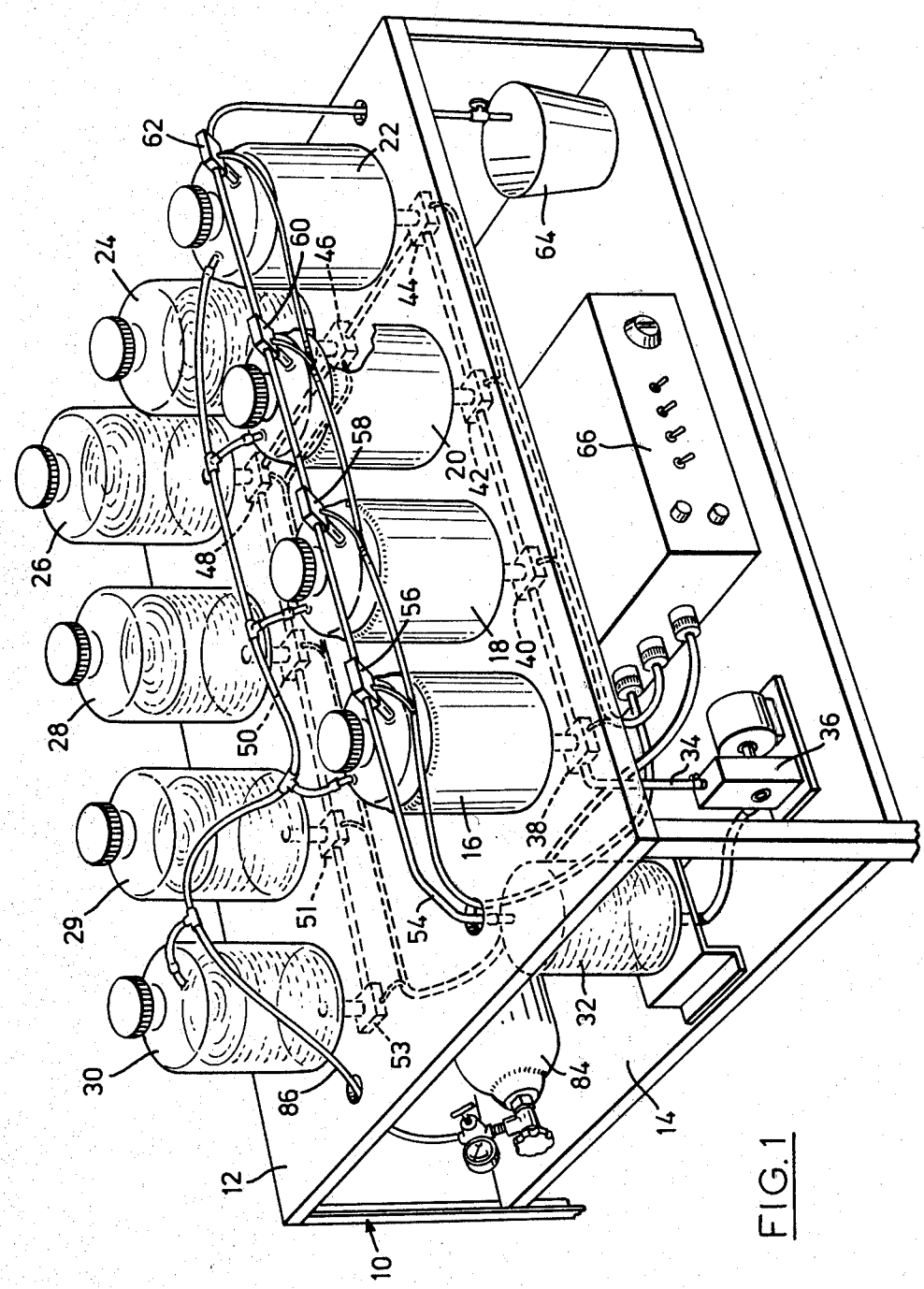
FIG. 1 is a general perspective view of the apparatus.

With reference to FIG. 1, the apparatus generally comprises a supporting frame 10 with an upper shelf 12 and a lower shelf 14. The upper shelf 12 carries nine reagent storage vessels in the form of sealed bottles, each having a lower outlet conduit. Bottles 16, 18, 20 and 22 each contain a different nucleotide reagent, and are provided wity refrigeration jackets to maintain the contents therein at low temperature, −35° C. Bottle 24 contains a capping reactant. Bottle 26 contains a deprotecting reagent. Bottle 28 contains an oxidizing reagent. Bottles 29 and 30 contain solvents. The lower shelf 14 carries a reaction column 32 in which polymer-nucleotide solid complexes are contained and in which reactions take place.

Figure 2:
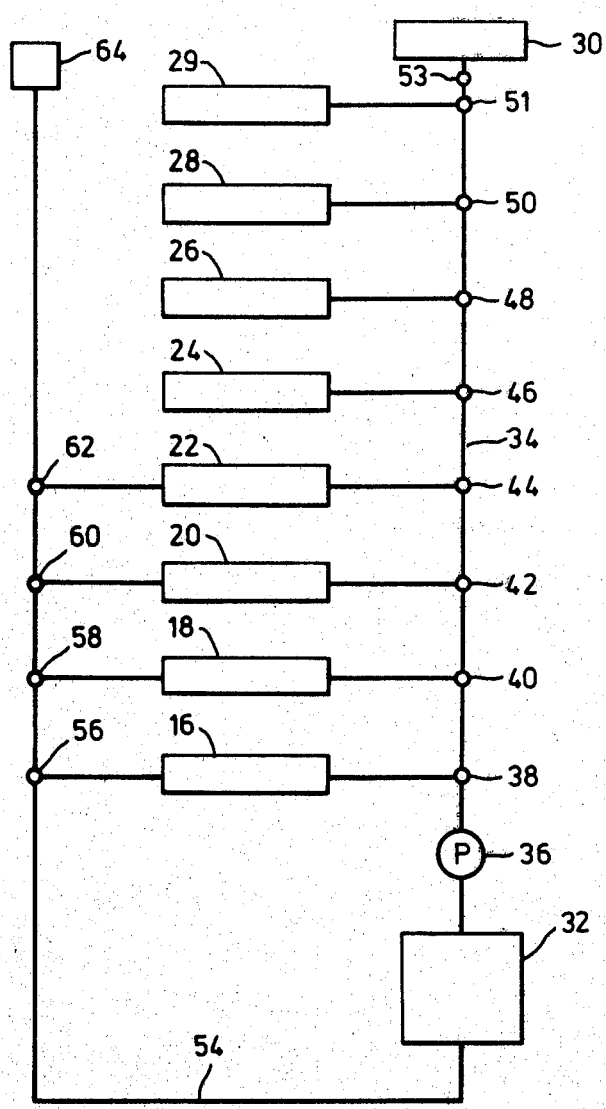
FIG. 2 is a diagrammatic fluid circuit diagram of the apparatus of FIG. 1.

A fluid flow conduit 34 feeds into the bottom of reaction column 32, via pump 36. Conduit 34 connects with each of the nine reagent storage vessels via a respective two-way valve 38, 40, 42, 44, 46, 48, 50, 51 and 52, and the lower outlet conduit thereof. Thus the reagent bottles and their valves are arranged in series. The order of reagent bottles in the downstream direction of the conduit 34 towards the pump 36 and reaction column 32 is thus solvent bottle 30, oxidizing reagent bottle 29, first deprotecting agent bottle 28, second deprotecting agent bottle 26, capping reactant bottle 24, and nucleotide reagent bottles 22, 20, 18 and 16 in that order. This arrangement is more clearly indicated diagrammatically in FIG. 2.

The top of reaction column 32 is provided with a re-cycle conduit 54 which connects serially with each of the nucleotide reagent bottles 22, 20, 18, 16, in that order, via respective two-way valves 62, 60, 58 and 56. No re-cycle connection is made to the remaining reagent bottles. Re-cycle conduit 54 terminates in a drain 64.

Figure 3:
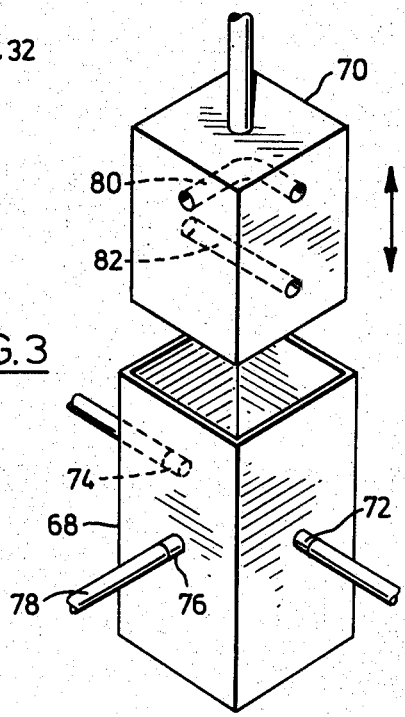
FIG. 3 is an exploded perspective view of a two-way valve used in the apparatus of FIGS. 1 and 2.

All of the various two-way valves are of essentially the same construction, diagrammatically illustrated in FIG. 3, biased towards a "straight through" position and solenoid operated. The lower shelf 14 also carries a microprocessor 66 connected to each of the two-way valves, permitting them to be moved to their appropriate settings automatically at predetermined times and for set periods.

The structure and operation of each valve 38, etc., is illustrated in FIG. 3. Each valve has a hollow, cylindrical valve housing 68 and a solid cylindrical valve member 70 which is a snug sliding fit therein. The housing 68 is provided with a pair of diametrically opposed ports 72, 74 connected to downstream and upstream parts of the fluid flow conduit 34 respectively, and a third port 76 at right angles to the other two, connected to the lower outlet conduit 78 from its respective reagent storage vessel 16, etc. All three ports 72, 74, 76 are in the same diametric plane of the housing 68. The valve member 70 has two separate and discreet passageways therethrough, disposed in different diametric planes. The first passageway or flow path 80 is right angular and, with the valve member 70 at the correct disposition in valve housing 68, puts port 76 into fluid communication with port 72, to allow flow of reagent from vessel 16, etc. into conduit 34. The second passageway or flow path 82 is linear and, with valve member 70 at its correct disposition in valve housing 68, puts port 74 into fluid communication with port 72, to allow straight through flow of reagent or solvent from an upstream storage vessel through conduit 34 towards the reaction column 32, under influence of the pump 30. The valves 38 etc. are all solenoid operated, upon receipt of signals from the microprocessor 66, and are biased towards their second position in which second, linear passageway 82 is in line with ports 72 and 74, and conduit 78 to the reagent storage vessel is sealed off.

The apparatus also includes a cylinder 84 containing dry nitrogen, from which gas flow lines 86 lead to nucleotide reagent bottles 16, 18, 20 and 22, and to solvent bottle 30. The nucleotide reagents and pyridine, the preferred solvent, are very sensitive to water and are thus suitably kept under an atmosphere of dry nitrogen.

A specific sequence of operations will now be described, as a specific, non-limiting example, with reference to the drawings.

The reaction column 32 contains derivatized silica gel, to which is coupled through an ester linkage 5′-dimethoxytrityl-1′-quanine-dioxyribose, this coupled product having been prepared exterially of the illustrated apparatus. This is a solid, finely divided, granular product. Nucleotide reagent bottle 16 contains 1'-thimine-5'-dimethoxytrityl-3'-metalphosphodichloridite-dioxyribose, in peridine solution. Reagent bottle 18 contains the corresponding 1'-guanine compoundin pyridine solution, reagent bottle 20 the corresponding 1'-adenine compound in pyridine solution and reagent bottle 22 the corresponding 1'-cytosine compound in pyridine solution. Each of bottles 16, 18, 20, 22 is kept at about −35° C. by refrigerant jackets, the solutions contained therein being liquid at such temperatures. Similarly, each bottle 16, 18, 20, 22 contains a dry nitrogen atmosphere, being connected to nitrogen cylinder 84 via open line 86. Reagent bottle 24 contains capping reagents, namely phenylisocyanate as a 0.5% solution in pyridine. Reagent bottle 26 contains the deprotecting agent trifluoroacetic acid (TFA) as a 1% solution in chloroform. Bottle 28 contains an oxydizing agent, namely iodine in water. Bottle 29 contains chloroform as wash liquid/solvent. Bottle 30 contains pyridine, as wash liquid/solvent. The pyridine in bottle 30 is kept under a nitrogen atmosphere, to keep it dry.

All of the valves 40, etc. through the respective bottles can connect with infeed conduit 34 are of the type illustrated in FIG. 3, solenoid operated from an external electric power source, and controlled by micro processor 66. They are biased to the "straight through" position, in which they do not permit any of the reagents from the respective vessels to the conduit 34 and hence to column 32. Thus, in the off, no-power position, pyridine solvent/wash liquid from bottle 30 connects into conduit 34 and column 32.

The operational sequence to prepare a polynucleotide of predetermined units sequence is fed into microprocessor 66 and the power is turned on, actuating pump 36. The first step is to deprotect the 5' position of the product in the column, so that firstly valve 48 is opened to pump in TFA from bottle 26. This reaction takes five minutes, at the expiry of which time the micro processor arranges return of valve 48 to its straight through position, and puts valve 51 to the open position to flush chloroform through the conduit 34 and column 32 to remove residual TFA. This stage of the process is of 15 minutes duration. This is followed by a pyridine wash, in which all valves are in the straight through mode, to prepare for the chain extension step.

Next, a 5' protected nucleotide base unit, from one of the downstream reagent bottles 16, 18, 20, 22, is fed to the column as selected by the micro processor. For example, the preselected base may the thymine derivative, in which case all valves except 38 are set to the straight through mode by the micro processor, and valve 38 is open to allow reagent from bottle 16 to be pumped into the column 32. This reaction continues for 40 minutes. At the same time, re-cycle valve 56 may be set to allow re-cycle of thymine reagent from the column to bottle 16. At the termination of this step of the process, both valves 38 and 56 are returned to their straight through modes.

The next stage is oxidation of the phosphite group of the just added reagent to phosphate. This is accomplished by opening valve 50 so that iodine/water mixture from bottle 28 is fed into the colum 32 via conduit 34. This stage lasts 10 minutes. Then valve 50 is returned to its straight through position, and valve 46 is opened to feed phenylisocyanatepyridine solution to the conduit 34 and the column 32. This reagent has the effect of removing the remains of the oxidationreagents, drying the polymer supported product and associated structure elements, and also to some extent capping off free hydroxyl groups on the polymer or product which might otherwise become involved in subsequent reaction steps and lead to byproduct formation. This stage lasts 20 minutes. Next, valve 51 is opened to allow chloroform from bottle 29 to wash through the system, to remove residual pyridine and phenylisocyanate residues. This stage lasts 10 minutes. Now the sequence can be repeated, starting with deprotection with reagent from bottle 26, and choosing another (or the same) phosphorylated, protected, sugar-base reagent from one bottles 16, 18, 20 and 22.

It will be appreciated that, during any given process stage, all valves, or all valves except one, in the conduit 34 are in their straight through mode, and it is assured by suitable hook-up to the microprocessor 66 that not more than one of such valves can be in other than the straight through mode at any given time. Thus, and in view of the valve structures previously described, no cross-contamination of reagents or formation of harmful byproducts can occur. The wrong reagents from any one of bottles 16, 18, 20, 22, 24, 26, 28, 29 and 30 cannot get into the inlet conduit 34 or the column 32 at the wrong time. The avoidance of communicating dead space in the valves themselves, coupled with appropriate washing steps, ensures that residues of reagents from previous process steps are not left in position where they can enter into subsequent reactions. It is similarly arranged that not more than one re-cycle valve 56, 58, 60 and 62 can be in other than its straight through mode at any given time also, and that such valve can only be set to its respective reagent bottle when its corresponding valve 38, 40, 42 or 44 is similarly open to its reagent vessel. At other times and stages, reagents from column 32 proceed via line 54 to drain 64.

Also, all of the valves are biased towards their straight through position. Thus in the event of a power failure or other malfunction, all valves in conduit 34 immediately assume a position allowing pyridine solvent wash to enter the full length of conduit 34 and column 32. This has the effect of protecting whatever product has been made in column 32, and preventing harmful and wasteful degradation thereof. Upon restoration of normal power, the reaction sequence can be readily resumed to produce the original predetermined product. If such malfunction occurs during chain extension or phenylisocyanate wash, the process can merely be resumed where it left off, since both steps take place in the presence of pyridine. If malfunction occurs during oxidation, it is necessary to resume by allowing the iodine-water oxidizing agent first to flush out the pyridine wash and then proceed with the oxidation reaction. If malfunction occurs during deprotection with TFA, the process must be re-started with a repeat of the earlier stage, namely chloroform wash, before deprotection is removed.

Thus the apparatus of the present invention provides a means for readily, simply and reliably producing polynucleotides of predetermined base unit sequences, in a semi-automatic manner, and ensuring against accidental formation of potentially disastrous byproducts. The apparatus is simple to maintain, construct and operate. It provides the necessary features to safeguard against loss or destruction of valuable product as a result of accidental malfunction.

Whilst a specific embodiment of the invention has been described herein and illustrated in detail, it will be appreciated that the invention is not limited thereto.

Other modifications will be apparent to those skilled in the art. The scope of the present invention is limited only by the scope of the appended claims.

We claim:

1. Apparatus for the step-wise synthesis of polynucleotides by sequential feed of appropriate nucleotide and other reagents to a polymer-nucleoside solid complex for reaction therewith, the apparatus comprising:

a reaction column for receiving the solid complex and conducting reactions therewith;

a solvent receiving reservoir upstream of said column;

a fluid flow conduit extending from the solvent receiving reservoir to the reaction column;

a plurality of nucleotide reagent receiving reservoirs;

at least one reactant receiving reservoir;

a plurality of two-way valves serially arranged in said conduit, each one associated with the respective nucleotide reagent receiving reservoir or a respective reactant receiving reservoir;

each said valve having two exclusive and discreet flow paths therethrough and being disposable in a first position in which its first flow path is utilized to provide fluid communication from its respective associated reservoir to said conduit, and in a second position in which its second flow path is utilized to provide for flow of fluid from another, upstream reservoir through the valve in the downstream direction, and each said valve being biased towards its second said position;

pumping means for delivery of solvent and reagents to the reaction column via said conduit, said pumping means being located downstream of the valves.

2. Apparatus according to claim 1 further including interlock means for said valves arranged to ensure that not more than one of said valves is in its first said position at any given time.

3. Apparatus according to claim 2 further including a drain conduit from the downstream end of said column, to permit drain of solvent and spent reactants from said column to a drain.

4. Apparatus according to claim 3 wherein said drain conduit includes a plurality of serially arranged two-way re-cycle valves, each associated with the respective one of said nucleotide reagent receiving reservoirs, and adapted to provide selective re-cycle of unreacted nucleotide reagent from the column to its respective reservoir.

5. Apparatus according to claim 4 wherein each said re-cycle valve has two exclusive and discreet flow paths therethrough, and is disposable in a first position in which its first flow path is utilized to provide fluid communication from the drain conduit to the respective associated reservoir, and in a second position in which its second flow path is utilized to provide for flow of fluid from the column through the valve towards the drain, in a downstream direction.

6. Apparatus according to claim 5 wherein each said re-cycle valve is biased towards its second said position.

7. Apparatus according to claim 6 including four said nucleotide reagent receiving reservoirs and associated, serially arranged valves in the fluid flow conduit and valves in the drain conduit.

8. Apparatus according to claim 7 including three reactant receiving reservoirs with associated valves serially arranged in the fluid flow conduit.

9. Apparatus according to claim 8 wherein the valves associated with the reactant receiving reservoirs are serially arranged in the fluid flow conduit upstream from the valves associated with the nucleotide reagent receiving reservoirs.

* * * * *